(12) United States Patent
Battung et al.

(10) Patent No.: US 9,610,293 B2
(45) Date of Patent: Apr. 4, 2017

(54) CO-MICRONIZATION PRODUCT COMPRISING ULIPRISTAL ACETATE

(71) Applicant: LABORATOIRE HRA-PHARMA, Paris (FR)

(72) Inventors: Florian Battung, Paris (FR); Pierre-Yves Juvin, Nantes (FR); Jérôme Hecq, Camblanes et Meynac (FR); Aude Colin, Bordeaux (FR)

(73) Assignee: LABORATOIRE HRA-PHARMA, Paris (FR)

( * ) Notice: Subject to any disclaimer, the term of this patent is extended or adjusted under 35 U.S.C. 154(b) by 0 days.

(21) Appl. No.: 14/441,027

(22) PCT Filed: Nov. 7, 2013

(86) PCT No.: PCT/FR2013/052670
§ 371 (c)(1),
(2) Date: May 6, 2015

(87) PCT Pub. No.: WO2014/072646
PCT Pub. Date: May 15, 2014

(65) Prior Publication Data
US 2015/0290218 A1   Oct. 15, 2015

(30) Foreign Application Priority Data

Nov. 8, 2012 (FR) ...................... 12 60603

(51) Int. Cl.
*A61K 31/57* (2006.01)
*A61K 47/20* (2006.01)
*A61K 9/16* (2006.01)

(52) U.S. Cl.
CPC .............. *A61K 31/57* (2013.01); *A61K 9/16* (2013.01); *A61K 47/20* (2013.01)

(58) Field of Classification Search
CPC ........... A61K 31/57; A61K 47/20; A61K 9/16
See application file for complete search history.

(56) References Cited

U.S. PATENT DOCUMENTS

| 4,895,726 A | 1/1990 | Curtet et al. |
| 2007/0042038 A1 | 2/2007 | Besse |
| 2009/0192130 A1 | 7/2009 | Nieman et al. |

FOREIGN PATENT DOCUMENTS

| EP | 2471537 | 7/2012 |
| WO | 9740823 | 11/1997 |
| WO | 00/28970 | 5/2000 |
| WO | 2008037044 | 4/2008 |
| WO | 2008/083192 A2 * | 7/2008 |
| WO | 2008079245 | 7/2008 |
| WO | 2009095418 | 6/2009 |
| WO | 2010066749 | 6/2010 |
| WO | 2010119029 | 10/2010 |

OTHER PUBLICATIONS

International Search Report and Written Opinion issued in corresponding International Application No. PCT/FR2013/052670 on Jan. 28, 2014.
Spence et al.(2005) "Increased Dissolution Rate and Bioavailability Through Comicronization with Microcrystalline Cellulose", Pharmaceutical Development and Technology,10:451-460.
Saharan et al. (2008) "Ordered Mixing: Mechanism, Process ad Applications in Pharmaceutical Formulations", Asian Journal of Pharmaceutical Sciences, 3(6), 240-259.
Colin et al. (2010) "Precellys—24 as a useful screening Tool in Preformulation for Micronisation and Co-Micronisation of Small Quantities of Poorly Water-Soluble Pharmaceutical API" poster presented at the 2nd conference on Innovation in Drug delivery, Aix-en-Provence, France.

\* cited by examiner

*Primary Examiner* — Alma Pipic
(74) *Attorney, Agent, or Firm* — Leason Ellis LLP

(57) ABSTRACT

The subject of the present invention is a co-micronization product comprising an active ingredient selected from the group consisting of ulipristal acetate, a ulipristal acetate metabolite and mixtures thereof, and a pharmaceutically acceptable solid surfactant. The invention also relates to a pharmaceutical composition comprising said co-micronization product and to the therapeutic uses thereof.

17 Claims, 4 Drawing Sheets

CO-MICRONIZATION PRODUCT COMPRISING ULIPRISTAL ACETATE

FIELD OF THE INVENTION

Figure 1:
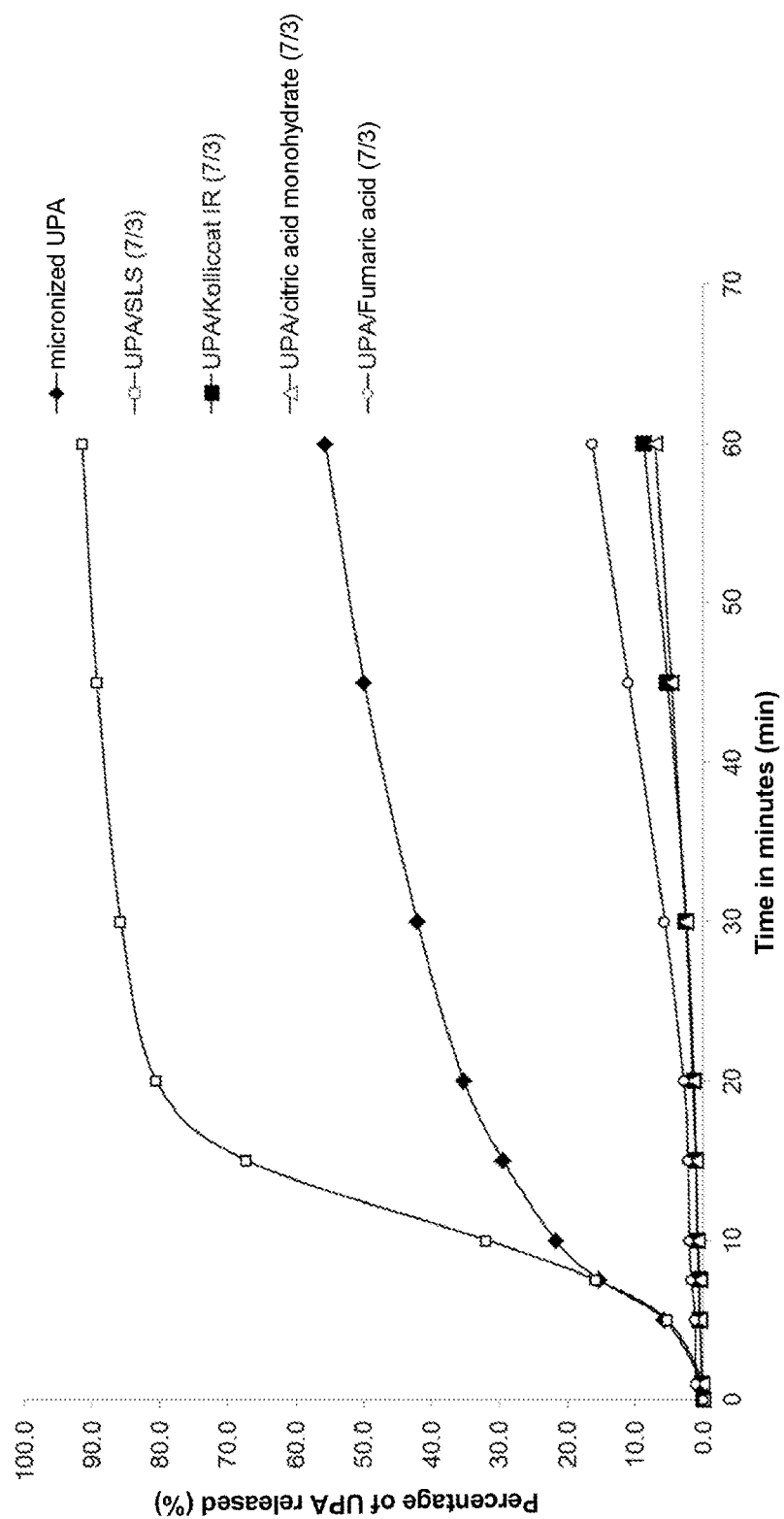

The present invention relates to a novel galenic form of ulipristal acetate, more specifically to a co-micronization product, and to pharmaceutical compositions containing said galenic form.

TECHNICAL BACKGROUND OF THE INVENTION

Ulipristal acetate (abbreviated as UPA) corresponds to 17α-acetoxy-11β-[4-(N,N-dimethylamino)-phenyl]-19-nor-pregna-4,9-diene-3,20-dione (IUPAC nomenclature) and has the following chemical formula:

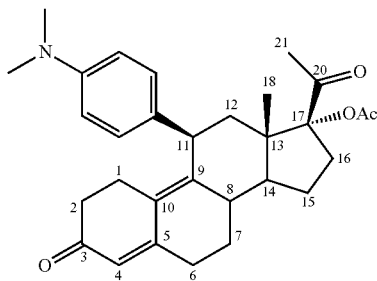

I

Its synthesis is described, inter alia, in patent EP 0 422 100 and in patent application EP 1 602 662.

Ulipristal acetate is a synthetic selective progesterone receptor modulator. By virtue of its action on the progesterone receptor, ulipristal acetate is capable of exerting a contraceptive action by inhibiting or delaying ovulation. Clinical studies showed that ulipristal acetate, administered in a single dose of 30 mg, makes it possible to prevent an unwanted pregnancy when it is administered within 120 hours following an unprotected or poorly protected sexual intercourse (Glasier et al., Lancet. 2010, 375(9714):555-62; Fine et al., Obstet Gynecol. 2010, 115:257-63). Ulipristal acetate has thus been authorized as an emergency contraceptive and is marketed under the trade name EllaOne® in Europe.

Other therapeutic applications of ulipristal acetate were proposed in the prior art. Recent clinical trials showed that the chronic administration of ulipristal acetate (at 5 mg or 10 mg per day) makes it possible to significantly reduce the symptoms associated with uterine fibromas and provides a therapeutic benefit which is greater than that of the reference treatment, namely leuprolide acetate (Donnez et al., N Engl J Med. 2012; 366(5):421-32). On the basis of these clinical trials, the European Medicines Agency (EMEA) authorized, in February 2012, the proprietary drug Esmya® (5 mg of ulipristal acetate) for the pre-operative treatment of symptoms associated with uterine fibromas.

The pharmaceutical compositions currently marketed comprise ulipristal acetate in a micronized form.

The proprietary drug Esmya® is provided in the form of a uncoated tablet comprising 5 mg of micronized ulipristal acetate combined with the following excipients: microcrystalline cellulose, mannitol, sodium croscarmellose, talc and magnesium stearate.

EllaOne® is, for its part, provided in the form of a uncoated tablet comprising 30 mg of micronized ulipristal acetate and the following excipients: lactose monohydrate, povidone K30, sodium croscarmellose and magnesium stearate.

Additional pharmaceutical compositions have been described in international application WO 2010/066749.

The development of new galenic forms suitable for the administration of ulipristal acetate remains a major challenge for therapeutic and contraceptive uses of ulipristal acetate.

In this regard, there is, at the current time, a need for new pharmaceutical formulations containing ulipristal acetate and having suitable release properties and a suitable bioavailability.

SUMMARY OF THE INVENTION

A subject of the present invention is a co-micronization product comprising (i) an active ingredient selected from the group consisting of ulipristal acetate, a metabolite of ulipristal acetate, and mixtures thereof, and (ii) a pharmaceutically acceptable solid surfactant.

In certain embodiments, the co-micronization product according to the invention has one or more of the following features:
 the weight ratio between the active ingredient and the surfactant is included in a range from 0.1 to 10, preferably 0.5 to 4,
 the surfactant is selected from $C_8$-$C_{20}$ alkyl sulphate salts and mixtures thereof, preferably sodium dodecyl sulphate,
 the active ingredient is selected from the group consisting of ulipristal acetate, 17α-acetoxy-11β-(4-N-methylaminophenyl)-19-norpregna-4,9-diene-3,20-dione, 17α-acetoxy-11β-(4-aminophenyl)-19-norpregna-4,9-diene-3,20-dione and mixtures thereof, and/or
 a d50 of less than 20 µm, preferably of less than 15 µm, and/or a d90 of less than 50 µm, preferably of less than 40 µm.

A subject of the present invention is also a method for preparing a co-micronization product as previously defined, comprising the steps consisting in:
 a) providing an active ingredient selected from the group consisting of ulipristal acetate, a ulipristal acetate metabolite and mixtures thereof,
 b) mixing the active ingredient of step a) with the surfactant and
 c) co-micronizing the mixture obtained in step b).

The active ingredient of step a) may be in micronized or non-micronized form.

An additional subject of the invention is a pharmaceutical composition comprising a co-micronization product as previously defined and a pharmaceutically acceptable excipient. The pharmaceutically acceptable excipient is preferably selected from the group consisting of a diluent, a binder, a flow agent, a lubricant, a disintegrant and mixtures thereof.

In certain embodiments, the pharmaceutical composition comprises:
 0.5% to 80% of co-micronization product,
 0% to 10% of disintegrant,
 15% to 95% of diluent, and
 0% to 5% of lubricant,
the percentages being expressed by weight relative to the total weight of the composition.

Preferably, the pharmaceutical composition according to the invention comprises from 1 mg to 100 mg, preferably from 1 mg to 40 mg, of active ingredient per dose unit. It is preferably intended to be administered orally and may be in the form of a powder, a granule, a film-coated or uncoated tablet, or a capsule.

A subject of the present invention is also a co-micronization product or a pharmaceutical composition, as previously defined, for use as a contraceptive, for example, as a regular contraceptive or as an emergency contraceptive.

Finally, a subject of the invention is also a co-micronization product or a pharmaceutical composition, as previously defined, for use in the treatment or prevention of a gynaecological disorder, preferably affecting the uterus.

FIGURES

FIG. 1 shows the in vitro dissolution curves for various comicronizates (see Example 1 hereinafter): UPA/SDS 7/3 (open square), UPA/kollicoat® IR 7/3 (solid square), UPA/citric acid monohydrate 7/3 (open triangle), UPA/fumaric acid 7/3 (open circle). Control experiment: micronized UPA (alone—in the absence of excipient) (solid diamond). y-axis: percentage of UPA released (%), x-axis: time in minutes.

Figure 2:
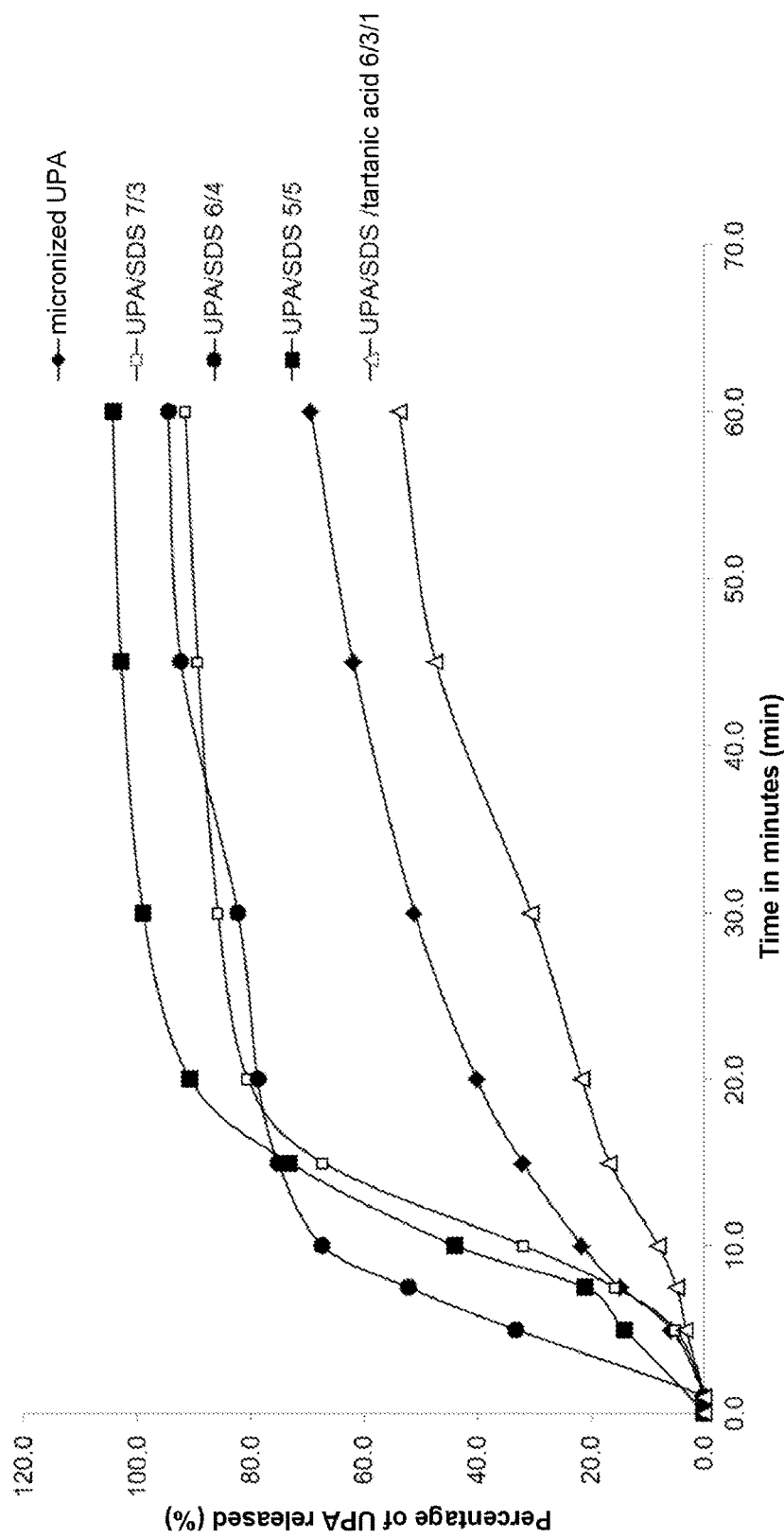

FIG. 2 shows the in vitro dissolution curves for various comicronizates (see Example 1 hereinafter): UPA/SDS 7/3 (open square), UPA/SDS 6/4 (solid circle), UPA/SDS 5/5 (solid square), UPA/SDS/tartaric acid 6/3/1 (open triangle), Control experiment: micronized UPA (alone—in the absence of excipient—(solid diamond)). y-axis: percentage of UPA released (%), x-axis: time in minutes.

Figure 3:
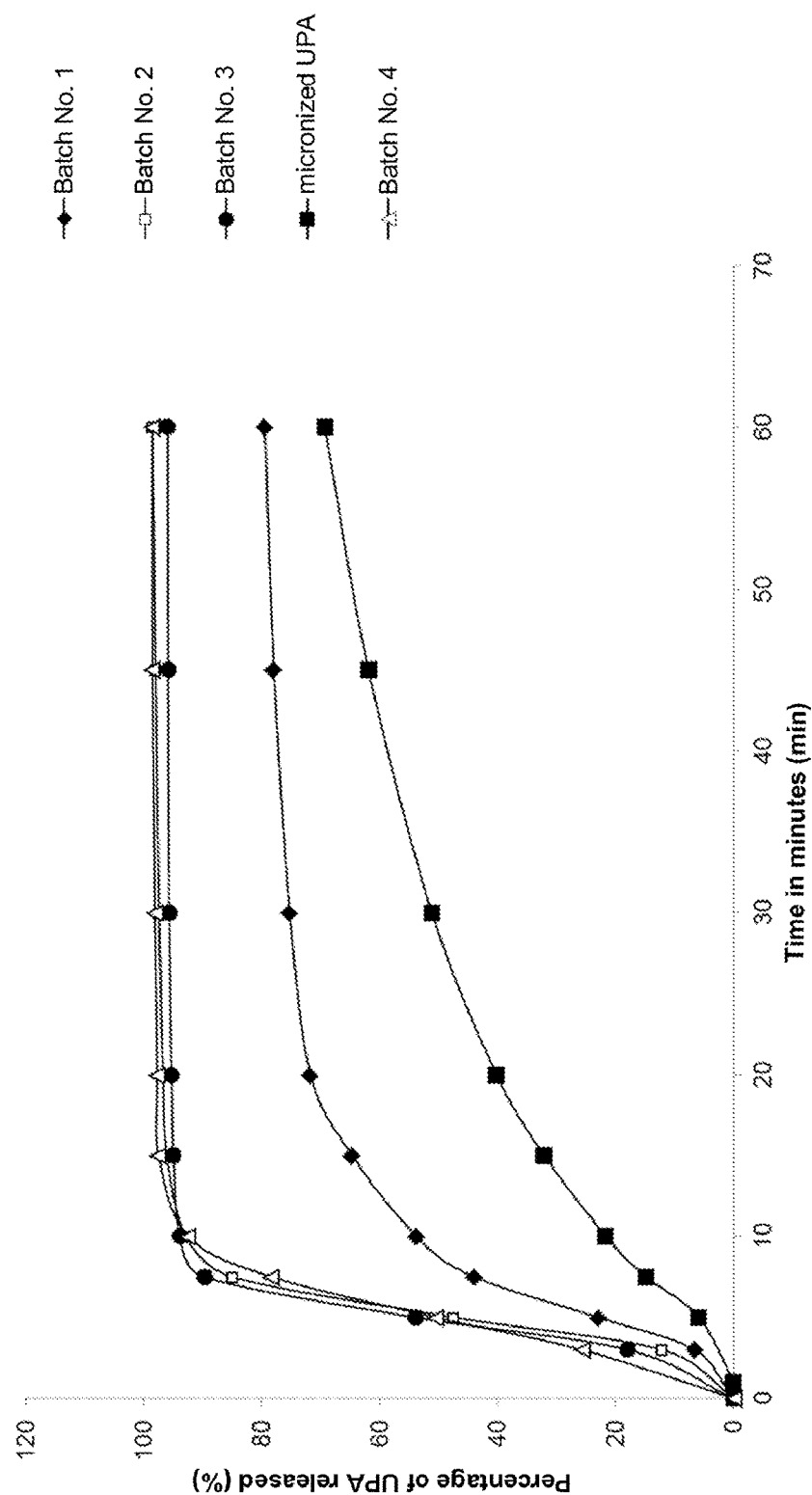

FIG. 3 shows the in vitro dissolution curves for various batches of UPA/SDS 1/1 comicronizates which differ in terms of their particle size distribution and/or the source of UPA (see Example 3 hereinafter): Batch No. 1 (solid diamond), batch No. 2 (open square), batch No. 3 (solid circle), batch No. 4 (open triangle), Control experiment: micronized UPA (alone—in the absence of excipient—(solid square)). y-axis: percentage of UPA released (%), x-axis: time in minutes.

Figure 4:
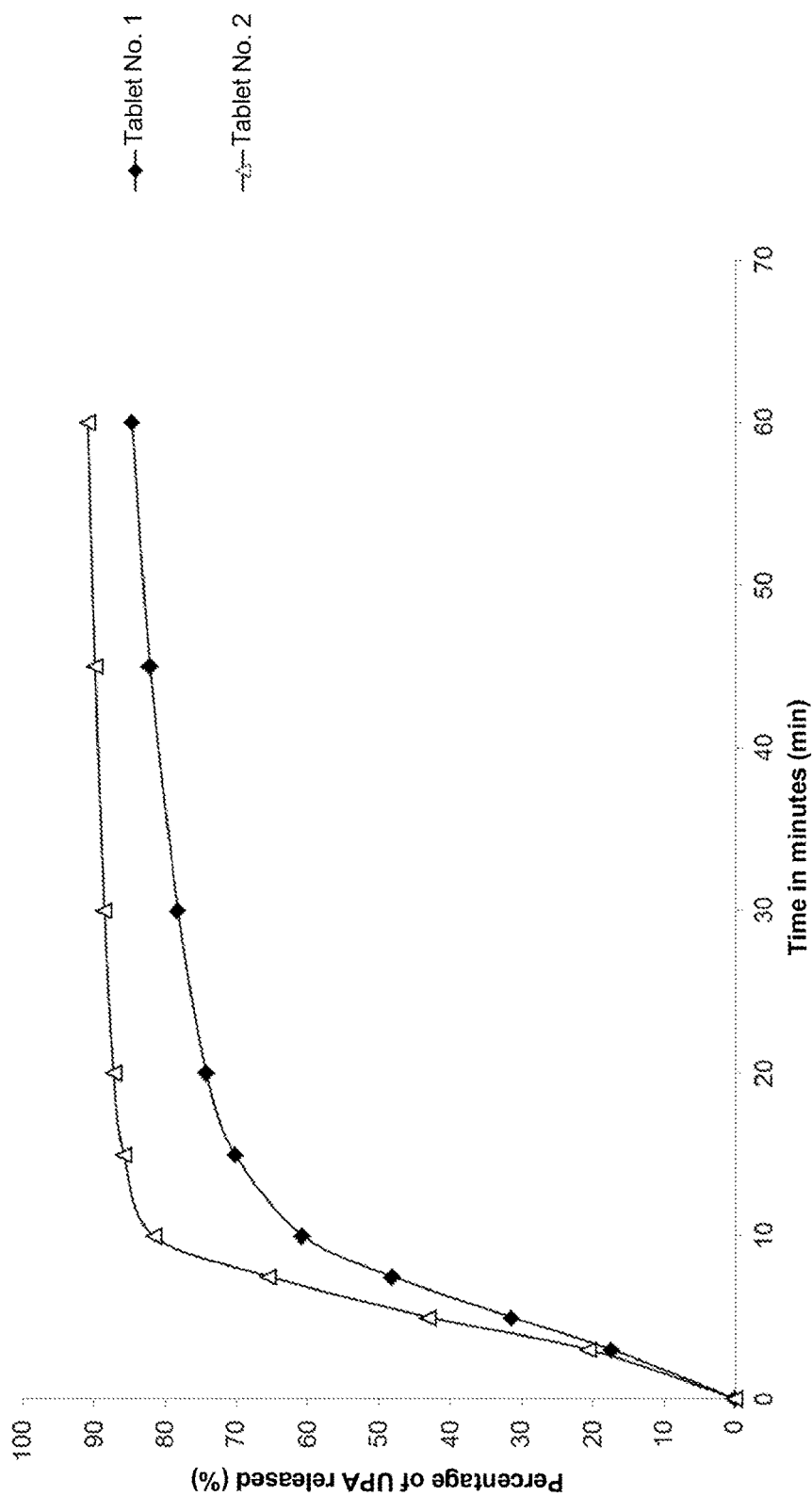

FIG. 4 shows the in vitro dissolution curves for tablets comprising the UPA/SDS 1/1 comicronizate (see Example 6 hereinafter): Tablet No. 1 (solid diamond), Tablet No. 2 (open triangle), y-axis: percentage of UPA released (%), x-axis: time in minutes.

DETAILED DESCRIPTION OF THE INVENTION

Co-Micronization Product According to the Invention and Preparation Method

At the end of lengthy research, the applicant showed that it is possible to significantly improve the in vitro dissolution and the in vivo bioavailability of ulipristal acetate (hereinafter UPA) by virtue of a co-micronization technology.

Surprisingly, the applicant showed that the product resulting from the co-micronization of ulipristal acetate with sodium dodecyl sulfate (also hereinafter called SDS or sodium lauryl sulfate) has an in vitro dissolution rate which is significantly higher than that of UPA micronized alone, in the absence of excipient. This increase in the dissolution rate of UPA is also observed when the co-micronization product is integrated into a pharmaceutical composition (see Example 6 hereinafter). The positive effect of the co-micronization on the properties of UPA was confirmed in vivo by pharmacokinetic studies conducted in animals by the applicant. These studies demonstrated that the UPA/SDS co-micronization product has a bioavailability and a rate of absorption for UPA which are higher than those observed for UPA in micronized form (see Example 5 hereinafter).

By virtue of its improved pharmacokinetic properties, the co-micronization product is expected to enable to reduce the doses of UPA to be administered in order to obtain the desired therapeutic or contraceptive effect. The decrease in the dose of UPA should make it possible, inter alia, to increase the safety, in particular the innocuousness, of the final pharmaceutical compositions. The applicant has shown that the dissolution rate and the pharmacokinetic properties of UPA in the co-micronization product are particularly improved when a surfactant, in particular sodium dodecyl sulphate, is used as comicronization excipient. Notably, the comicronization does not systematically result in an improvement of the dissolution properties of UPA. The comicronization excipients tested by the applicant in Example 1 hereinafter, which are not surfactants, have proved to be ineffective in improving the in vitro dissolution properties of UPA. In particular, contrary to what the skilled artisan could have anticipated with regard to the dissolution properties of UPA in an acidic medium, the micronization of UPA with an organic acid has led to a clear decrease in the in vitro dissolution rate (see Example 1 hereinafter). Moreover, the applicant has demonstrated that the product obtained by intimate mixing of SDS and micronized UPA exhibits in vitro dissolution properties which are inferior to those of the product resulting from the co-micronization of said mixture (see Example 2), even after incorporation into a pharmaceutical composition (see Example 6). All of these results emphasize that the improvement in the dissolution properties of UPA in the comicronizates results from the specific combination (i) of the co-micronization technology and (ii) of the use of a surfactant, in particular SDS, as co-micronization excipient.

Thus, a subject of the present invention is a novel galenic form, more specifically a co-micronization product comprising:

an active ingredient selected from the group consisting of ulipristal acetate, a ulipristal acetate metabolite and mixtures thereof, and a pharmaceutically acceptable solid surfactant.

The term "co-micronization product" (also hereinafter denoted comicronizate) is intended to mean the product obtained by micronizing a mixture comprising an active ingredient and at least one excipient. In the case in point, it is a solid mixture in the form of a powder.

In the context of the present invention, the term "micronization" is intended to mean a method which makes it possible to reduce the size of the particles of a powder, for example by milling. The reduction in the size of the particles is evidenced by a decrease of at least 10% of a parameter selected from the d50, the d10 and the d90. A reduction of "at least 10%" encompasses a reduction of at least 20%, of at least 30%, of at least 40% and of at least 50%.

The micronization can be carried out by means of commercially available devices, such as ball or air jet micronizers.

In the context of the present invention, the term "a micronized product" is intended to mean a product which is in the form of a powder having a d90 of less than 50 μm. Thus, preferably, the co-micronization product according to the invention has a d90 of less than 50 μm.

UPA metabolites are described, inter alia, in Attardi et al., Journal of Steroid Biochemistry and Molecular Biology, 2004, 88: 277-288 and illustrated hereinafter:

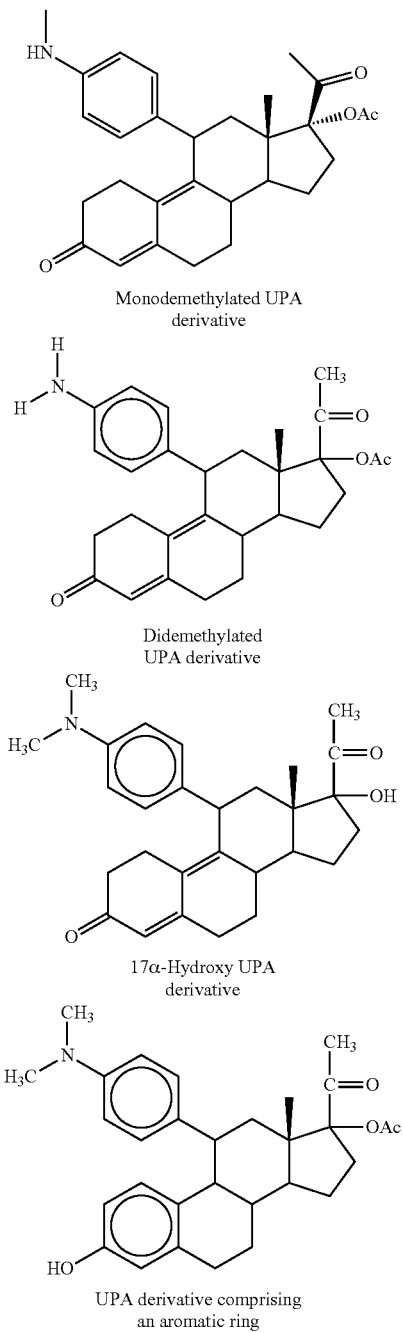

Monodemethylated UPA derivative

Didemethylated UPA derivative

17α-Hydroxy UPA derivative

UPA derivative comprising an aromatic ring

Preferably, the ulipristal acetate metabolite is selected from:
17α-acetoxy-11β-(4-N-methylaminophenyl)-19-nor-pregna-4,9-diene-3,20-dione (monodemethylated derivative) and
17α-acetoxy-11β-(4-aminophenyl)-19-norpregna-4,9-diene-3,20-dione (didemethylated derivative).

In one preferred embodiment of the comicronizate according to the invention, the active ingredient is selected from the group consisting of 17α-acetoxy-11β-(4-N-methylaminophenyl)-19-norpregna-4,9-diene-3,20-dione, 17α-acetoxy-11β-(4-aminophenyl)-19-norpregna-4,9-diene-3, 20-dione, ulipristal acetate and mixtures thereof.

The pharmaceutically acceptable surfactant is preferably selected from the surfactants commonly used in galenics which can undergo co-micronization, and mixtures thereof. The term "solid surfactant" is intended to mean a surfactant which is solid at ambient temperature, i.e. typically at approximately 20° C. In certain advantageous embodiments, the surfactant has a high melting point, preferably above 50° C. and even more preferably above 100° C.

Preferably, the surfactant is selected from $C_8$-$C_{20}$, preferably $C_{10}$-$C_{14}$, alkylsulfate salts, and mixtures thereof.

In one advantageous embodiment, the surfactant is selected from the dodecyl sulfate salts, preferably the alkali metal or alkaline-earth metal salts thereof, such as a sodium, magnesium or calcium salt.

As is exhaustively demonstrated by the examples of the present application, a surfactant that is particularly suitable for obtaining a co-micronization product according to the invention is SDS, i.e. sodium dodecyl sulfate, also known as sodium lauryl sulphate (abbreviated as SLS). Thus, in a preferred embodiment, the surfactant is sodium dodecyl sulphate.

In other embodiments, the co-micronization product according to the invention comprises:
an active ingredient selected from the group consisting of from the group consisting of 17α-acetoxy-11β-[4-N-methylaminophenyl)-19-norpregna-4,9-diene-3,20-dione, 17α-acetoxy-11β-[4-aminophenyl)-19-norpregna-4,9-diene-3,20-dione, ulipristal acetate and mixtures thereof, preferably ulipristal acetate, and
sodium dodecyl sulphate as co-micronization excipient.

The weight ratio between the active ingredient and the surfactant is generally included in a range from 0.1 to 10, preferably from 0.5 to 4. An active ingredient/surfactant weight ratio of from 0.5 to 4 encompasses a weight ratio of from 0.5 to 1, from 1 to 1.5, from 1.5 to 2, from 2 to 2.5, from 3 to 3.5, and from 3.5 to 4.

Preferably, the active ingredient/surfactant weight ratio is included in a range from 0.8 to 2.5. A suitable active ingredient/surfactant weight ratio is, for example, a weight ratio ranging from 0.8 to 1.2, such as a weight ratio of 1.

As has been shown in the examples, the particle size distribution (i.e. the distribution of the size of the particles) of the co-micronization product can have an effect on the UPA solubility properties. It is preferable for the d50 of the co-micronization product to be less than 25 μm, preferably less than 20 μm, or even less than 15 μm.

A d50 of less than 15 μm encompasses a d50 of less than 12 μm, than 11 μm, than 10 μm, than 9 μm, than 8 μm, than 7 μm, than 6 μm, than 5 μm, and than 4 μm. It is also preferable for the d90 of the co-micronization product to be less than 50 μm, or even less than 40 μm. A d90 of less than 40 μm encompasses a d90 of less than 38 μm, than 37 μm, than 36 μm, than 35 μm, than 34 μm, than 33 μm, than 32 μm, than 31 μm, than 30 μm, than 29 μm, than 28 μm, than 27 μm, than 26 μm, than 25 μm, than 24 μm, than 23 μm, then 22 μm, than 21 μm, than 20 μm, than 19 μm, than 18 μm, than 17 μm, than 16 μm, than 15 μm, than 14 μm, than 13 μm, than 12 μm, than 11 μm, and than 10 μm.

In certain embodiments, the co-micronization product according to the invention is characterized in that its particle size distribution has:
a d50 of less than 20 μm, preferably less than 15 μm, and/or
a d90 of less than 50 μm, preferably less than 40 μm and even more preferably less than 30 μm.

By way of example, the comicronizate according to the invention may have a d50 of less than 5 μm and/or a d90 of less than 15 μm.

The d10 of the comicronizate according to the invention is generally greater than 0.05 µm.

In the context of the present invention, "a d50 of less than X µm" means that at least 50% of the comicronizate particles have a size of less than X µm.

"A d90 of less than Y µm" means that at least 90% of the comicronizate particles have a size of less than Y µm.

Likewise, "a d10 of greater than Z µm" means that at least 90% of the comicronizate particles have a particle size greater than Z µm.

The granulometry—i.e. the distribution of the size of the particles—of the co-micronization product, and in particular the d90, d50 and d10 parameters, can be determined by any method known to those skilled in the art. Preferably, laser diffraction will be used. Example 3 hereinafter proposes conditions for implementing this method.

In certain embodiments, the comicronizate may comprise one or more excipients in addition to the surfactant. The additional excipient(s) may be selected from a diluent, a binder, a disintegrant and mixtures thereof. In certain embodiments, the additional excipient(s) is (are) polymeric. By way of example, they may be selected from N-vinyl-2-pyrrolidone polymers and copolymers, such as a copovidone, a povidone or a crospovidone.

In certain particular embodiments, the comicronizate according to the invention comprises:
   an active ingredient selected from the group consisting of ulipristal acetate, a ulipristal acetate metabolite and mixtures thereof,
   a pharmaceutically acceptable solid surfactant, preferably SDS, and
   an additional excipient selected from the group consisting of N-vinyl-2-pyrrolidone polymers and copolymers and mixtures thereof, preferably a crospovidone, a povidone and mixtures thereof.

The additional excipient may be present in an amount corresponding to an "active ingredient/additional excipient" weight ratio of from 0.1 to 10, preferably from 0.5 to 4.

In one additional embodiment, the comicronizate is devoid of additional excipient, i.e. devoid of an excipient other than the surfactant. In particular, the comicronizate according to the invention may consist of the active ingredient and the surfactant.

As is illustrated in the examples, the comicronization product has improved properties in terms of bioavailability and in vitro dissolution of the active ingredient. In certain embodiments, the comicronization product according to the invention is characterized in that at least 80% of the active ingredient that it contains is released within 30 minutes when said comicronization product is subjected to an in vitro dissolution test, preferably as defined in the European Pharmacopoeia §2.9.3.

The in vitro dissolution test can be carried out using any commercially available device comprising paddles. Example 1 hereinafter presents implementing conditions for determining the in vitro dissolution rate of a comicronizate according to the invention. Briefly, an amount of comicronizate representing 30 mg of active ingredient is placed in a gelatin gel capsule. This gel capsule is then placed in 900 ml of a medium buffered at gastric pH, comprising 0.1% of SDS, at 37±0.5° C., and subjected to stirring at 50 revolutions per minute (rpm) (speed of rotation of the paddles of the dissolution device).

The dissolution of the active ingredient in the medium can be monitored by spectrophotometry at the maximum wavelength of absorbance. A gastric pH is typically a pH of 1 to 3.

A subject of the present invention is also a method for preparing the comicronizate described above comprising the steps consisting in:
   a) providing an active ingredient selected from the group consisting of ulipristal acetate, a ulipristal acetate metabolite and mixtures thereof,
   b) mixing the active ingredient of step a) with a pharmaceutically acceptable surfactant and
   c) micronizing the mixture obtained in step b).

As shown in the examples, the active ingredient provided in step a) may be in micronized or non-micronized form. Moreover, the active ingredient may be amorphous or crystalline. Preferably, the active ingredient provided in step a) is in a crystalline form.

The surfactant used in step b) may be non-micronized or micronized.

The micronization step c) may be carried out using a commercially available micronization system. It may in particular be an air jet micronizer or a ball micronizer. Those skilled in the art, by virtue of their general knowledge and the performing of routine experiments, will be able to determine the conditions for carrying out step c) in order to obtain a co-micronization product having the desired particle size distribution. By way of example, when step c) is carried out using an air-jet micronizer, the skilled artisan will be able to vary the powder feed flow and the pressure of the air jets in order to modulate the particle size distribution of the final comicronizate.

Pharmaceutical Composition According to the Invention

The comicronization product is intended mainly for therapeutic or contraceptive use. For this purpose, it can be administered directly or inserted into an administration device such as a vaginal ring, a patch, an intrauterine device or an implant.

Generally, the co-micronization product according to the invention is integrated into a pharmaceutical composition so as to facilitate its administration. Thus, an additional subject of the present invention is a pharmaceutical composition comprising a co-micronization product as previously defined and at least one pharmaceutically acceptable excipient.

The skilled artisan will be able to choose the excipient(s) to be combined with the co-micronization product according to the final form of the pharmaceutical composition, the desired route of administration and the desired active ingredient release profile. For this purpose, the skilled artisan will be able to refer to the following reference works: Remington: The Science and Practice of Pharmacy (Lippincott Williams & Wilkins; Twenty first Edition, 2005) et, Handbook of Pharmaceuticals Excipients, American Pharmaceutical Association (Pharmaceutical Press; 6th revised edition, 2009).

The pharmaceutical composition and the comicronizate according to the invention may be administered by any route, in particular the oral, buccal, nasal, sublingual, vaginal, intra-uterine, rectal or transdermal route or by the parenteral route, for example by intravenous injection. The preferred routes of administration are the buccal, oral, intra-uterine and vaginal routes.

The pharmaceutical composition according to the invention may be in any form, for example in the form of a tablet, a powder, a capsule, a pill, a suppository, a vaginal suppository, a suspension, an aqueous, alcoholic or oily solution, a syrup, a gel, an ointment, an emulsion, a lyophilizate or an orodispersible film. The route of administration and the galenic form of the pharmaceutical composition may depend on the desired therapeutic or contraceptive effect.

In certain embodiments, the pharmaceutical composition according to the invention may be integrated into a device enabling prolonged administration of the active ingredient. The pharmaceutical composition may in particular be incorporated into a vaginal ring, into an intrauterine device, into a patch, for example a transdermal or mucoadhesive patch, or into an implant, for example an implant of contraceptive type. For examples of vaginal rings suitable for implementing the invention, reference may be made to application WO 2006/10097.

In additional embodiments, the pharmaceutical composition according to the invention is in solid form. Preferably, the pharmaceutical composition according to the invention is solid and is intended for oral administration.

In certain embodiments, the pharmaceutical competition according to the invention is characterized in that the pharmaceutically acceptable excipient is selected from the group consisting of a diluent, a binder, a flow agent, a lubricant, a disintegrant and mixtures thereof.

For the purposes of the present invention, a diluent may be one or more compounds capable of densifying the active ingredient so as to obtain the desired mass. The diluents encompass inorganic phosphates, monosaccharides and polyols such as xylitol, sorbitol, lactose, galactose, xylose or mannitol, disaccharides such as sucrose, oligosaccharides, polysaccharides such as cellulose and its derivatives, starches, and mixtures thereof. The diluent may be in anhydrous or hydrated form.

By way of example, a suitable diluent may be selected from microcrystalline cellulose, mannitol, lactose and mixtures thereof.

The binder may be one or more compounds capable of improving the aggregation of the active ingredient with the diluent. By way of example of binders, mention may be made of hydroxypropylcellulose, hydroxypropylmethylcellulose, povidone (polyvinylpyrrolidone), copolymers of N-vinyl-2-pyrrolidone and of vinyl acetate (copovidone), and mixtures thereof.

The lubricant may be one or more components capable of preventing the problems associated with the preparation of dry galenic forms, such as the sticking and/or gripping problems which occur in machines during compression or filling. The preferred lubricants are fatty acids or fatty acid derivatives, such as calcium stearate, glyceryl monostearate, glyceryl palmitostearate, magnesium stearate, zinc stearate, or stearic acid, polyalkylene glycols, in particular polyethylene glycol, sodium benzoate or talc. The lubricants that are preferred according to the invention are the stearate salts and mixtures thereof. A suitable lubricant is, for example, magnesium stearate.

The flow agent optionally used according to the invention may be selected from compounds which contain silicon, for example talc, anhydrous colloidal silica or precipitated silica.

The disintegrant can be used to improve the release of the active ingredient. It may be selected, for example, from crosslinked polyvinylpyrrolidone (crospovidone), crosslinked carboxymethylcellulose (such as sodium croscarmellose) or non-crosslinked carboxymethylcellulose, starches and mixtures thereof. The disintegrant is preferably selected from the group consisting of a sodium croscarmellose, a crospovidone and mixtures thereof.

In certain embodiments, the composition according to the invention comprises:
    0.5% to 80% of the co-micronization product as previously defined,
    0% to 10% of disintegrant,
    15% to 95% of diluent, and
    0% to 5% of lubricant,
the percentages being expressed by weight relative to the total weight of the composition.

The composition according to the invention may in addition be characterized in that it comprises from 0% to 20% by weight of a binder, and from 0% to 5% by weight of a flow agent.

In other embodiments, the composition according to the invention comprises:
    1% to 65% of the co-micronization product as previously defined,
    0% to 10% of disintegrant, preferably selected from a sodium croscarmellose, a crospovidone and mixtures thereof,
    25% to 95% of diluent, preferably selected from mannitol, lactose, microcrystalline cellulose and mixtures thereof, and
    0% to 5% of lubricant, preferably a stearate, such as magnesium stearate,
the percentages being expressed by weight relative to the total weight of the composition.

In one additional embodiment, the composition according to the invention comprises:
    1% to 45% of the comicronization product,
    0% to 10% of disintegrant, preferably selected from a sodium croscarmellose, a crospovidone and mixtures thereof,
    40% to 95% of diluent, preferably selected from mannitol, lactose, microcrystalline cellulose and mixtures thereof, and
    0% to 3% of lubricant, preferably a stearate, such as magnesium stearate.

By way of example, the pharmaceutical composition according to the invention may comprise from:
    1% to 10% by weight of the co-micronization product,
    80% to 95% by weight of diluent,
    1% to 8% by weight of disintegrant, and
    0.1% to 2% of a lubricant,
the percentages being expressed by weight relative to the total weight of the composition.

A further example is a pharmaceutical composition comprising from:
    35% to 45% by weight of co-micronization product,
    50% to 60% by weight of diluent,
    1% to 8% by weight of disintegrant, and
    0.1% to 2% of a lubricant,
the percentages being expressed by weight relative to the total weight of the composition.

It goes without saying that, in the examples described above, the co-micronization product preferably comprises ulipristal acetate as active ingredient and sodium dodecyl sulphate as surfactant according to a weight ratio of 0.8 to 2.5.

The pharmaceutical composition according to the invention may also comprise one or more excipients in addition to the above mentioned excipients. The additional excipient(s) may be selected from the group consisting of coating agents, such as coating agents based on polyvinyl alcohol or on hydroxypropylmethylcellulose, pigments such as aluminium oxide or iron oxide, flavourings, wetting agents, waxes, dispersants, stabilizers and preservatives.

In certain embodiments, the pharmaceutical composition according to the invention is free of binder and/or of flow agent. In other embodiments, the SDS present in the co-micronization product is the only surfactant present in the pharmaceutical composition.

The pharmaceutical composition according to the invention may be prepared according to any one of the methods commonly used in galenics. These methods typically comprise mixing the co-micronization product according to the invention with one or more excipients, then shaping the mixture obtained. By way of example, when it is in the form of a tablet, the pharmaceutical composition according to the invention can be prepared by direct compression or by compression after dry or wet granulation.

In the embodiments described above of the pharmaceutical composition according to the invention, the co-micronization product is preferably characterized in that it comprises UPA and SDS, the UPA/SDS weight ratio being from 0.5 to 4, preferably from 0.8 to 2.5. It goes without saying that the co-micronization product integrated into the pharmaceutical composition according to the invention may have any one of the characteristics described in the present description. In particular, the comicronization product has one or more (1, 2, 3, 4 or 5) of the following characteristics:

i. the active ingredient is UPA and the surfactant is SDS,
ii. the active ingredient/surfactant weight ratio is from 0.8 to 1.2,
iii. the d50 of the co-micronization product is less than 20 µm, preferably less than 15 µm,
iv. the d90 of the co-micronization product is less than 50 µm, preferably less than 40 µm, and
v. at least 80% of the active ingredient that the co-micronization product contains is released within 30 minutes when said co-micronization product is subjected to an in vitro dissolution test, preferably under the following conditions:
   device: paddle dissolution device,
   sample: gelatin gel capsule containing an amount of comicronizate corresponding to 30 mg of active ingredient,
   dissolution medium: 900 ml of an aqueous solution buffered at gastric pH comprising 0.1% of SDS,
   temperature: 37±0.5° C., and
   paddle rotation speed: 50 revolutions per minute (rpm).

Another further example according to the invention is a pharmaceutical composition comprising from:

4% to 10% by weight of co-micronization product according to the invention, preferably comprising UPA and SDS in a UPA/SDS weight ratio of from 0.8 to 2.5, preferably from 0.8 to 1.2,
50% to 65% by weight of microcrystalline cellulose and from 25% to 35% by weight of mannitol as diluents,
1% to 8% by weight of crospovidone and/or of sodium croscarmellose as disintegrant, and
0.1% to 2% of magnesium stearate as lubricant.

As previously mentioned, the composition according to the invention may be in the form of a powder, a granule, a film-coated or non-film-coated tablet, or a gel capsule, and is preferably intended for oral administration. In certain embodiments, the pharmaceutical composition according to the invention is in the form of a non-film-coated tablet intended for oral administration.

The composition according to the invention may be a controlled-, immediate-, sustained- or delayed-release pharmaceutical composition. Preferably, the composition according to the invention is an immediate-release composition.

The term "immediate-release composition" is intended to mean a pharmaceutical composition characterized in that at least 75% of the active ingredient initially contained in a dose unit of the pharmaceutical composition is released within 45 minutes when said dose unit is subjected to an in vitro dissolution test, for example as defined in the European Pharmacopoeia §2.9.3, and preferably under the following conditions:

paddle dissolution device,
dissolution medium: aqueous solution buffered at gastric pH containing 0.1% of SDS,
temperature: 37±0.5° C., and
rotation speed: 50 rpm.

The volume of the dissolution medium depends on the amount of active ingredient contained in the dose unit. For a dose unit comprising 5 mg of active ingredient, 500 ml of dissolution medium are used. For a dose unit comprising 30 mg of active ingredient, 900 ml of dissolution medium are used.

In certain embodiments, the composition according to the invention is characterized in that at least 60%, or even at least 70%, of the active ingredient present in a dose unit is released within 20 minutes, when said dose unit is subjected to an in vitro dissolution test preferably carried out under the conditions described above.

The expression "at least 70% of the active ingredient present in a dose unit" encompasses at least 72%, at least 74%, at least 76%, at least 78%, at least 80%, at least 82%, and at least 86% of the active ingredient present in a dose unit.

In certain embodiments, the composition according to the invention is characterized in that at least 80% of the active ingredient present in a dose unit is released within 20 minutes, when said dose unit is subjected to an in vitro dissolution test preferably carried out under the conditions described above.

Generally, the pharmaceutical composition comprises from 1 mg to 100 mg of active ingredient per dose unit, preferably from 1 mg to 40 mg, or even from 2 mg to 30 mg, of active ingredient per dose unit. The dose of active ingredient depends on the therapeutic or contraceptive effect and on the administration scheme that are desired. For example, for certain applications, the amount of UPA per dose unit may be included in a range from 1 mg to 5 mg.

In emergency contraception, the active ingredient may be present in an amount of from 20 mg to 40 mg per dose unit.

In regular contraception, the active ingredient may be present in an amount of from 2 mg to 5 mg per dose unit.

For therapeutic uses such as the treatment of uterine fibromas, the active ingredient may be present in an amount of from 3 mg to 15 mg per dose unit.

The dose of active ingredient and the administration scheme may also depend on the personal parameters of the patient, in particular the weight, age, sex, general health condition and diet, on the pathological conditions from which the patient is suffering, etc.

Finally, the pharmaceutical composition according to the invention may comprise an additional active ingredient. This additional active agent may exert an action different from that of UPA or its metabolites. It may also reinforce the therapeutic effect of UPA or its metabolites.

Therapeutic or Contraceptive Uses of the Comicronizate and of the Pharmaceutical Composition According to the Present Invention In an additional aspect, a subject of the present invention is also a co-micronization product or a pharmaceutical composition as previously described, for use as a medicament. The co-micronization product or the composition according to the invention is particularly suitable for use as a regular contraceptive or an emergency contraceptive. It can also be used for the treatment or prevention of hormonal, gynaecological or endocrine disorders, such as Cushing's disease. The composition or the comicronization product according to the invention can be used, in particular, in the treatment or prevention of a gynaecological disorder, preferably affecting the uterus, including benign gynaecological disorders. The gynaecological disorders encompass, without being limited thereto, uterine fibromas and symptoms thereof, adenomyosis, endometriosis, pain associated with endometrium dislocation, and excessive uterine bleeding.

An additional subject of the invention is the use of the co-micronization product according to the invention for preparing a contraceptive or for preparing a medicament intended for the treatment or prevention of any one of the abovementioned pathological conditions.

A subject of the invention is also a method of contraception comprising the administration, to a patient, of a contraceptive dose of the co-micronization product or of the pharmaceutical composition according to the invention.

The term "method of contraception" is intended to mean a method which makes it possible to prevent the occurrence of a pregnancy in a patient of child-bearing age.

In the case in point, it may be a method of emergency contraception. In this case, a single dose is preferably administered to the patient within an appropriate time period after unprotected or poorly protected sexual intercourse, generally within 120 h following unprotected or poorly protected sexual intercourse.

The method of contraception may also be a method of regular contraception, in which the composition or the co-micronization product are administered chronically and cyclically to the patient or continuously using a device such as an implant or a vaginal ring.

By way of alternative, the method of contraception may be a method of "on demand" contraception as described in international application WO 2010/119029.

Finally, a subject of the invention is also a method for treating a disease or a disorder in a patient, comprising the administration of a therapeutically effective dose of the co-micronization product or of the pharmaceutical composition according to the invention to a patient, preferably a female patient. The therapeutic method according to the invention preferably relates to any one of the abovementioned diseases or disorders.

It goes without saying that, for the implementation of the methods and uses described above, the co-micronization product and the pharmaceutical composition according to the invention may comprise one or more of the characteristics explained in detail in the present description.

The objective of the examples hereinafter is to illustrate the invention more fully without, however, limiting the scope thereof.

EXAMPLES

Example 1

Screening of Excipients for the Co-Micronization of Ulipristal Acetate (UPA)

1. Materials and Methods

Preparation of Comicronizates

The ulipristal acetate comicronization products (hereinafter "comicronizates") were prepared according to the following method: The ulipristal acetate and the comicronization excipient to be tested were mixed in the desired weight ratio in a mortar and triturated until a homogeneous mixture was obtained. The mixture obtained was then micronized in a ball mill-homogenizer.

In Vitro Dissolution of the UPA Comicronizates

For each comicronizate obtained, hard gelatin gel capsules containing an amount of comicronizate corresponding to 30 mg of UPA per capsule were prepared. The studies of in vitro dissolution of UPA as comicronizate were carried out using these capsules according to the European Pharmacopoeia in §2.9.3, using a paddle dissolution device. For each comicronizate, a gel capsule containing said comicronizate was placed in a bowl of the dissolution device containing 900 ml of a dissolution medium. The dissolution medium is an aqueous solution buffered at gastric pH and comprising 0.1% by weight of SDS. The conditions for carrying out the in vitro dissolutions are the following:

Paddle rotation speed: 50 revolutions per minute (rpm)
Temperature: 37° C.±0.5° C.

The dissolution of the UPA was monitored by spectrophotometry.

By way of control experiment, a gelatin gel capsule containing 30 mg of ulipristal acetate micronized alone (i.e. UPA micronized in the absence of any co-micronization excipient) was used.

For each comicronizate, the dissolution experiment was reproduced 3 times.

2. Results

Screening of Comicronization Excipients

Table 1 below and FIG. 1 show the dissolution results obtained for each comicronizate prepared. The dissolution percentages are expressed relative to the initial amount of UPA contained in each gel capsule.

TABLE 1

Results of the in vitro dissolution assays for the UPA/excipient comicronizates prepared. UPA/excipient weight ratio 7/3. Control experiment: UPA micronized alone.

Percentages of UPA released, expressed relative to the initial amount of UPA contained per gel capsule (Mean values over 3 experiments)

| Time (min) | UPA micronized alone | UPA/SDS | UPA/Kollicoat ® IR | UPA/citric acid monohydrate | UPA/fumaric acid |
|---|---|---|---|---|---|
| 0 | 0.0 | 0.0 | 0.0 | 0.0 | 0.0 |
| 1 | 0.0 | 0.0 | 0.2 | 0.1 | 1.1 |
| 5 | 5.5 | 5.3 | 0.5 | 0.5 | 1.2 |
| 7.5 | 15.00 | 15.8 | 0.7 | 0.6 | 1.8 |
| 10 | 22.30 | 31.9 | 0.9 | 0.8 | 2.1 |
| 15 | 30.00 | 67.3 | 1.1 | 1.1 | 2.3 |
| 20 | 34.30 | 80.5 | 1.4 | 1.6 | 2.9 |
| 30 | 39.50 | 85.8 | 2.5 | 2.6 | 5.7 |
| 45 | 47.50 | 89.3 | 5.3 | 4.7 | 11.0 |
| 60 | 53.80 | 91.5 | 8.8 | 7.1 | 16.4 |

It is specified that Kollicoat IR® is a polyethylene glycol/polyvinyl alcohol grafted copolymer.

These results show that the comicronization of ulipristal acetate with sodium dodecyl sulfate (SDS) makes it possible to very significantly improve the dissolution rate and the final amount of UPA released. Notably, the percentage of ulipristal acetate released into the dissolution medium at t=20 min is approximately 80% for a gel capsule comprising the UPA/SDS comicronizate, whereas it is only approximately 35% for a gel capsule containing ulipristal acetate which has been micronized in the absence of excipient.

The comicronizate of UPA with Kollicoat IR® has a UPA release rate which is much lower than that observed for the micronized UPA since, after 60 min, less than 10% of the UPA initially contained in the comicronizates has been released.

As is illustrated in Table 2 below, the solubility of the ulipristal acetate decreases very significantly according to the pH of the medium. It was therefore expected that the comicronization of ulipristal acetate with an acidic excipient—such as citric acid or fumaric acid—would make it possible to improve the dissolution of ulipristal acetate by decreasing the pH in the close surroundings of the dosage form and therefore by locally increasing its solubility.

TABLE 2

UPA solubility as a function of pH

| pH | UPA solubility (g/l) |
|---|---|
| 1.2 | 22.7 |
| 4.5 | 0.039 |
| 6.8 | 0.005 |

Surprisingly, contrary to what might have been expected with regard to the solubility of UPA in an acidic medium, the co-micronization of UPA with an organic acid leads to a clear decrease in the UPA dissolution rate.

Conclusion

The comicronization in the presence of SDS made it possible to significantly increase the UPA dissolution rate and release rate in vitro compared with UPA in micronized form. On the other hand, contrary to what might have been expected, the other comicronization excipients tested in Example 1 had a clearly negative impact on UPA release. The increase in the dissolution rate is therefore a specific effect of the SDS.

Influence of the UPA/SDS Weight Ratio on the In Vitro Dissolution of UPA

Various UPA/SDS comicronizates were prepared according to the comicronization method described above in order to study the influence of the UPA/SDS weight ratio on the in vitro dissolution rate of UPA. By way of comparison, a UPA/SDS/tartaric acid comicronizate in a 6/3/1 weight ratio was prepared in order to confirm the effect of a comicronization excipient of organic acid type on the dissolution of UPA.

The in vitro dissolutions obtained are illustrated in FIG. 2 and presented in Table 3 hereinafter.

TABLE 3

In vitro dissolution of UPA as a function of the UPA/SDS weight ratio of the comicronizates. Control experiments: UPA micronized alone and UPA/SDS/tartaric acid comicronizate in a 6/3/1 molar ratio Percentages of UPA released, expressed relative to the initial amount of UPA contained per gel capsule (Mean values over 3 experiments)

| Time (min) | Micronized UPA (in the absence of excipient) | comicronizate UPA/SDS 7/3 | UPA/SDS 6/4 | UPA/SDS 5/5 | UPA/SDS/tartaric acid 6/3/1 |
|---|---|---|---|---|---|
| 0.0 | 0.0 | 0.0 | 0.0 | 0.0 | 0.0 |
| 1.0 | 0.0 | 0.0 | 0.2 |  | 0.0 |
| 5.0 | 5.5 | 5.3 | 33.4 | 14.2 | 3.4 |
| 7.5 | 15.00 | 15.8 | 52.2 | 21.1 | 5.0 |
| 10.0 | 22.30 | 31.9 | 67.4 | 44.0 | 8.3 |
| 15.0 | 30.00 | 67.3 | 75.2 | 73.2 | 16.8 |
| 20.0 | 34.30 | 80.5 | 78.8 | 90.7 | 21.7 |
| 30.0 | 39.50 | 85.8 | 82.3 | 99.0 | 30.6 |
| 45.0 | 47.50 | 89.3 | 92.3 | 102.9 | 47.4 |
| 60.0 | 53.80 | 91.5 | 94.5 | 104.4 | 53.9 |

Conclusion

The UPA dissolution rate increases with the decrease in the UPA/SDS weight ratio. The presence of a small proportion of tartaric acid in the comicronizate has a negative impact on the UPA dissolution rate which is not completely compensated by the presence of the SDS. This confirms the results obtained previously with fumaric acid and citric acid.

Other Examples of Comicronizate

A UPA/SDS/crospovidone comicronizate was prepared by comicronization of an intimate mixture of SDS, UPA and crospovidone in the weight ratios 5/2/3 using a ball mill-homogenizer. The in vitro dissolution profile is determined as described in point 1. above.

TABLE 4

UPA/crospovidone/SDS (5/2/3) comicronizate. Percentages of UPA released, expressed relative to the initial amount of UPA contained per gel capsule (Mean values over 3 experiments)

| Time (min) | % UPA released |
|---|---|
| 0 | 0.0 |
| 1 | 0.4 |
| 5 | 7.1 |
| 7.5 | 18.0 |
| 10 | 28.0 |
| 15 | 58.3 |
| 20 | 67.6 |
| 30 | 80.7 |
| 45 | 85.4 |
| 60 | 86.8 |

Example 2

Comparison of the Dissolution Profile of a UPA/SDS Comicronizate Compared with a UPA/SDS Mixture 1. Materials and Methods The ulipristal acetate and the SDS were mixed in a 1/1 weight ratio in a mortar and triturated until a homogeneous mixture was obtained. A part of the mixture obtained was introduced into hard gelatin gel capsules in a proportion of 60 mg per gel capsule (i.e. 30 mg of UPA per gel capsule).

The remaining mixture was co-micronized using an air-jet micronizer (Alpine AS 200 jet mill). Hard gelatin gel capsules were filled with 60 mg of the final comicronizate (i.e. an amount of UPA of 30 mg/capsule).

The dissolution of the UPA for the two types of capsules was studied under conditions and in a dissolution medium identical to those of Example 1.

2. Results

The dissolutions obtained for the UPA/SDS comicronizate and the non-micronized UPA/SDS mixture (physical mixture) are illustrated in Table 5 below.

TABLE 5

In vitro dissolution of UPA in the dissolution medium of Example 1 using a comicronizate UPA/SDS 1/1 and a physical mixture (not co-micronized) UPA/SDS 1/1. Percentages of UPA released, expressed relative to the initial amount of UPA contained in each gel capsule (Mean values over 3 experiments)

| Time (min) | Comicronizate UPA/SDS 1/1 | physical mixture UPA/SDS 1/1 |
|---|---|---|
| 0 | 0 | 0 |
| 3 | 29.6 | 32.2 |
| 5 | 69.3 | 61 |
| 7.5 | 86.2 | 68.4 |
| 10 | 94.3 | 71.8 |
| 15 | 96.4 | 76.2 |
| 20 | 96.8 | 79.3 |
| 30 | 97.4 | 83.4 |
| 45 | 97.9 | 86.9 |
| 60 | 98.1 | 88.8 |

The dissolution rate of the UPA is significantly higher for the comicronizate than for the physical mixture after 20 minutes. This result shows that the comicronization has a direct impact on the in vitro dissolution of the UPA.

Example 3

Effect of the Source of UPA and of the Granulometry of the Comicronizate on the UPA Dissolution Rate 1. Materials and Methods Preparation of Comicronizates The comicronizates of ulipristal acetate with SDS were prepared using an air jet micronizer.

Briefly, the ulipristal acetate and the SDS were mixed in a 1/1 weight ratio in a mortar and triturated until a homogeneous mixture was obtained.

The mixture obtained was micronized in a micronizer (Fluid Energy Loop Mill) according to the following conditions:

Feed flow rate: 3 gr/min

Venturi Pressure: 40 PSI

Mill Pressure from 10 to 120 PSI according to the desired particle size distribution.

The mill pressure was modulated so as to modify the granulometry of the final comicronizate. The granulometry—i.e. the distribution of the size of the particles—of the resulting comicronizates was determined by a laser diffraction (Equipment: Malvern—Mastersizer 2000SM Scirocco 2000, optical model: Fraunhofer). The comicronizates were prepared either from micronized ulipristal acetate, or from non-micronized ulipristal acetate. Table 6 hereinafter presents the granulometry of the batches of comicronizates obtained as a function of the UPA source and the mill pressure.

TABLE 6

Particle size distribution of the various co-comicronizates UPA/SDS 1/1

| Batch No. | UPA source | D10 (μm) | D50 (μm) | D90 (μm) |
|---|---|---|---|---|
| 1 | Non-micronized | 2.54 | 21.35 | 143.89 |
| 2 | | 0.79 | 3.32 | 10.03 |
| 3 | | 0.69 | 2.48 | 6.00 |
| 4 | micronized | 0.51 | 1.36 | 3.76 |

In Vitro Dissolution

For each batch of comicronizate, hard gelatin capsules comprising 60 mg of comicronizate (i.e. 30 mg of UPA per gel capsule) were prepared. The dissolution profiles were obtained under the conditions described in Example 1.

2. Results

Effect of the UPA Source

FIG. 3 shows the dissolution curve for the UPA/SDS comicronizate obtained from non-micronized UPA (batch No. 3, FIG. 3: solid circle) and that of the UPA comicronizate obtained from a micronized UPA source (batch No. 4, FIG. 3: open triangle). It should be noted that the two comicronizates have a similar granulometry (see batches No. 3 and No. 4—Table 6). The two dissolution profiles show that the nature of the starting UPA—micronized or non-micronized—has no effect on the dissolution properties of the final comicronizate.

Effect of the Granulometry of the Comicronizate on UPA Release

Table 7 below and FIG. 3 illustrate the in vitro dissolution results obtained for the various batches of comicronizate.

TABLE 7

In vitro dissolution results obtained for the batches of comicronizates

| | Percentages of UPA released, expressed relative to the initial amount of UPA contained per gel capsule (Mean values over 3 experiments) | | |
|---|---|---|---|
| Time (min) | Batch No. 3 | Batch No. 2 | Batch No. 1 |
| 0 | 0 | 0 | 0 |
| 3 | 18 | 12.2 | 6.7 |
| 5 | 54.1 | 47.4 | 23.0 |
| 7.5 | 89.7 | 85.0 | 44.0 |
| 10 | 93.9 | 92.9 | 53.9 |
| 15 | 95 | 96.1 | 64.7 |
| 20 | 95.3 | 96.8 | 71.8 |
| 30 | 95.7 | 97.4 | 75.3 |
| 45 | 95.9 | 98.0 | 78.0 |
| 60 | 96 | 98.5 | 79.5 |

It appears that the dissolution rate and the final degree of dissolution of the UPA for batches No. 3 (FIG. 3, solid circle) and No. 2 (FIG. 3, empty square) are higher than for batch No. 1 (FIG. 3, solid diamond). This shows that the granulometry of the comicronizate can have an effect on the UPA dissolution rate.

For information, it will be noted that comicronizate No. 1, despite its coarse granulometry, has a UPA dissolution rate which is much higher than that observed for the UPA micronized alone (i.e. in the absence of co-micronization excipient). This confirms, once again, the specific effect of the co-micronization in the presence of SDS on the in vitro dissolution properties of UPA.

Example 5

Pharmacokinetic Studies in Rats

The objective of this study is to illustrate that the co-micronization of ulipristal acetate with SDS makes it possible to improve the pharmacokinetic profile, in particular the bioavailability, of the UPA in comparison with micronized UPA.

1. Materials and Methods

Animals

The pharmacokinetic study was carried out on female OFA(SD) rats weighing between 0.206 and 0.251 kg. The animals were deprived of food for 16 hours before the administration of the samples. The animals were placed in cages, the temperature of which was maintained between 20 and 25° C.; the day/night cycles were 12 h each (6 am-6 pm) and the air was conditioned using a ventilation system.

UPA Samples

The samples tested are the following:

Comicronizate of ulipristal acetate/SDS, 1/1 ratio

Powder of ulipristal acetate micronized in the absence of any excipient (UPA micronized alone)

Administration Protocol

A predetermined amount of powder was administered by means of an oesophageal tube using a cannula. The powder was introduced into the stomach of each animal using a catheter. The dose administered corresponds to 4 mg of ulipristal acetate per kg.

Taking Samples

Blood samples of 300 µl were taken from the (left or right) jugular of the rats. In order to avoid excessively high blood sampling, the rats were divided into 3 groups of 6 rats as follows:

TABLE 8

Sampling schedule

| Sampling time | Rat groups | | |
|---|---|---|---|
| | No. 1 | No. 2 | No. 3 |
| Pre-administration (Time = 0) | x | | |
| 10 min | x | | |
| 15 min | | x | |
| 20 min | | | x |
| 30 min | x | | |
| 45 min | | | x |
| 1 h | | x | |
| 1.25 h | x | | |
| 1.5 h | | | x |
| 2 h | | x | |
| 2.5 h | | | x |
| 3 h | | x | |
| 4 h | | | x |
| 6 h | | | x |
| 10 h | | x | |
| 16 h | x | | |
| 24 h | x | | |
| 36 h | | x | |

The samples were collected on heparin tubes and then centrifuged within the hour for 7-8 min at 1600 g at 4° C. At each sampling time, the plasma of the 6 rats of the group is "pooled".

Methods for Assaying the UPA in the Plasma Samples

The ulipristal acetate was assayed by LC/MS/MS under the following conditions:

Mobile phase: Methanol/distilled water (70/30, V/V)+1% acetic acid

Column: BDS Hypersil phenyl, 100×2.1 mm, 5 µm

Elution mode: isocratic flow rate: 0.400 ml/min

Injection volume: 10.0 µl

Needle cleaning liquid: Acetonitrile/isopropanol/acetone (40/40/20, V/V/V)

2. Results

Table 9 below presents the pharmacokinetics results obtained. The co-micronization makes it possible to increase the bioavailability of the UPA: The $AUC_{0-t}$ and the $AUC_{0-inf}$ for the comicronizate are approximately 15% to 20% higher than the AUCs obtained for the micronized UPA. The UPA absorption rate is also faster with the comicronizate ($T_{max}$=1 h) than with the micronized UPA ($T_{max}$=1.25 h). Notably, the comicronization does not significantly increase the $C_{max}$ (variation of +3.6% only). These in vivo results are coherent with the in vitro dissolution results previously obtained.

TABLE 9

Pharmacokinetics results

| | comicronizate UPA/SDS 1/1 | Micronized UPA | Variations |
|---|---|---|---|
| Cmax (ng/ml) | 463 | 447 | +3.6% |
| Tmax (h) | 1.0 | 1.25 | −20% |
| AUC0-t (h · ng/ml) | 1595 | 1340 | +19% |
| AUCinf (h · ng/ml) | 1610 | 1383 | +16.4% |

In conclusion, the comicronization in the presence of SDS makes it possible to significantly improve the bioavailability of the UPA, without however drastically increasing the Cmax.

The comicronization of UPA in the presence of SDS makes it possible to obtain a novel matrix of active ingredient with improved bioavailability, which should make it possible to reduce the doses of UPA to be administered to the patient in order to achieve the desired therapeutic effects. This novel matrix should also make it possible to develop new UPA administration schemes.

Example 6

Pharmaceutical Compositions Integrating the Comicronizate According to the Invention 1. Materials and Methods In order to confirm the gain in UPA dissolution, even after formulation of the comicronizate, tablets containing 5 mg of ulipristal acetate (non-film-coated) were produced by direct compression and tested under the same in vitro dissolution conditions as those described in Example 1, with the exception of the volume of the dissolution medium, which in this case is 500 ml. The composition of the tablets is given in Table 10 below.

TABLE 10 composition of the tablets prepared

| | Tablet No. 1 (invention) | | Tablet No. 2 (invention) | |
|---|---|---|---|---|
| Ingredients | mg/tablet | % by weight | mg/tablet | % by weight |
| UPA/SDS 1/1 | 10.00 | 6.7 | 10.00 | 6.7 |
| Microcristalline cellulose | 92.45 | 61.6 | 87.50 | 58.3 |

TABLE 10-continued composition of the tablets prepared

| Ingredients | Tablet No. 1 (invention) mg/tablet | % by weight | Tablet No. 2 (invention) mg/tablet | % by weight |
|---|---|---|---|---|
| Mannitol | 43.50 | 29.0 | 43.50 | 29.0 |
| Sodium croscarmellose | 2.55 | 1.7 | 7.50 | 5.0 |
| Magnesium stearate | 1.50 | 1.0 | 1.50 | 1.0 |
| Total | 150.00 | 100.0 | 150.00 | 100.0 |

2. Results

The in vitro dissolution profiles are illustrated in FIG. 4 and presented in Table 11 below.

TABLE 11

Results of the in vitro dissolutions for tablets No. 1 and No. 2

| | Percentages of UPA dissolution | |
|---|---|---|
| Time (min) | Tablet No. 1 (invention) | Tablet No. 2 (invention) |
| 0 | 0 | 0 |
| 3 | 17.3 | 20.6 |
| 5 | 31.4 | 43.1 |
| 7.5 | 48.2 | 65.5 |
| 10 | 60.7 | 81.7 |
| 15 | 70.2 | 85.9 |
| 20 | 74.2 | 87.3 |
| 30 | 78.2 | 88.6 |
| 45 | 82.2 | 89.9 |
| 60 | 84.7 | 90.9 |

The tablets according to the invention exhibit high rates and a high final degree of UPA release. These results confirm that the co-micronization of UPA with SDS makes it possible to improve its solubilization properties, even after integration into a complex pharmaceutical composition.

Finally, during the preparation of the tablets, the applicant observed that the comicronizate product was much easier to formulate than the UPA micronized without SDS. Indeed, the applicant noted that the formulation used to prepare tablets No. 1 and No. 2 was fluid and easily compressible even in the absence of talc (flow agent) and of binder. In other words, the comicronizate according to the invention can be easily formulated, even in the absence of flow agent.

3. Comparative Tests 3 additional batches of tablets were prepared by direct compression. The batch of tablets No. 3 corresponds to the invention. The batches No. 4 and No. 5 correspond to comparative batches since they are free of comicronizate. Tablets No. 4 comprise micronized UPA and SDS, while tablets No. 5 comprise micronized UPA only.

TABLE 12

Examples of tablets

| Ingredients | Tablet No. 3 (invention) mg/tablet | Tablet No. 4 (comparative) mg/tablet | Tablet No. 5 (comparative) mg/tablet |
|---|---|---|---|
| Micronized UPA | 0 | 5 | 5 |
| SDS | 0 | 5 | 0 |
| comicronizate UPA/SDS 1/1 | 10 | 0 | 0 |
| Microcrystalline cellulose | 88.25 | 88.25 | 93.25 |
| Mannitol | 43.5 | 43.5 | 43.5 |
| Crospovidone | 7.5 | 7.5 | 7.5 |
| Magnesium stearate | 0.75 | 0.75 | 0.75 |
| TOTAL | 150 | 150 | 150 |

The in vitro dissolution profiles for these tablets were obtained according to the conditions described in point 1. above and are illustrated in Table 13 below.

TABLE 13

Results of the in vitro dissolutions for tablets No. 3 (invention), No. 4 (comparative) and No. 5 (comparative)

| | Percentages of UPA dissolution | | |
|---|---|---|---|
| Time (min) | Tablet No. 3 (invention) | Tablet No. 4 (comparative) | Tablet No. 5 (comparative) |
| 0 | 0 | 0 | 0 |
| 3 | 6.8 | 12.6 | 26.7 |
| 5 | 54.3 | 56.2 | 43 |
| 7.5 | 79.2 | 60.5 | 46 |
| 10 | 87.2 | 62.6 | 47.8 |
| 15 | 88.9 | 65.4 | 49.6 |
| 20 | 89.8 | 67.5 | 50.9 |
| 30 | 90.9 | 70.7 | 52.7 |
| 45 | 92.1 | 74.7 | 55.3 |
| 60 | 93.1 | 78.3 | 57.3 |

It appears that the rate and the final degree of dissolution of the UPA for the tablet according to the invention (tablet No. 3) are higher than those of tablet No. 4 (mixture of SDS and of micronized UPA) and of tablet No. 5 (micronized UPA).

These results confirm the specific effect of the comicronization in the presence of a surfactant, such as SDS, on the UPA solubilization properties, even after incorporation into a pharmaceutical composition.

For information, it is specified that the compositions according to the invention that are illustrated in Tables 10 and 12 can be used, for example, in regular contraception or on-demand contraception, or else as a medicament, for example for the treatment of gynaecological disorders such as uterine fibroma.

Example 7

Additional Examples of Compositions According to the Invention

Table 14 hereinafter presents an additional example of a composition according to the invention. This composition can be prepared and shaped by direct compression.

TABLE 14 additional example of a composition according to the invention

| Composition | mg/tablet | % by weight |
|---|---|---|
| comicronizate UPA/SDS 1/1 | 60 (of which 30 mg of UPA) | 40 |

TABLE 14-continued additional example of a composition according to the invention

| Composition | mg/tablet | % by weight |
|---|---|---|
| Microcrystalline cellulose | 38.25 | 25.5 |
| Mannitol | 43.5 | 29 |
| Crospovidone | 7.5 | 5 |
| Magnesium stearate | 0.75 | 0.5 |
| Total | 150 | 100 |

This composition can be used as an emergency contraceptive.

Other examples of tablets are provided hereinafter. These tablets can be prepared by direct compression.

| Composition | mg/tablet | % by weight |
|---|---|---|
| comicronizate UPA/SDS 1/1 | 60.0 (of which 30 mg of UPA) | 50 |
| Lactose | 49.2 | 41 |
| Crospovidone | 9.6 | 8 |
| Magnesium stearate | 1.2 | 1 |
| Total | 120.0 | 100 |

| Composition | mg/tablet | % by weight |
|---|---|---|
| comicronizate UPA/SDS 1/1 | 8.00 (of which 4 mg of UPA) | 12.5 |
| Lactose | 28.80 | 45 |
| Mannitol | 20.48 | 32 |
| Sodium croscarmellose | 6.40 | 10 |
| Magnesium stearate | 0.32 | 0.5 |
| Total | 64.00 | 100 |

| Composition | mg/tablet | % by weight |
|---|---|---|
| comicronizate UPA/SDS 1/1 | 20.0 (of which 10 mg of UPA) | 25 |
| Lactose | 32.0 | 40 |
| Microcrystalline cellulose | 22.4 | 28 |
| Crospovidone | 4.8 | 6 |
| Magnesium stearate | 0.8 | 1 |
| Total | 80.0 | 100 |

| Composition | mg/tablet | % by weight |
|---|---|---|
| comicronizate UPA/SDS 6/4 | 10.00 (of which 6 mg of UPA) | 6.7 |
| Microcristalline cellulose | 92.45 | 61.6 |
| Mannitol | 43.50 | 29 |
| Sodium croscarmellose | 2.55 | 1.7 |
| Magnesium stearate | 1.50 | 1 |
| Total | 150 | 100 |

| Composition | mg/tablet | % by weight |
|---|---|---|
| comicronizate UPA/SDS 7/3 | 42.85 (of which 30 mg of UPA) | 30.6 |
| Microcrystalline cellulose | 45.40 | 32.4 |
| Mannitol | 43.5 | 31.1 |
| Crospovidone | 7.5 | 5.4 |
| Magnesium stearate | 0.75 | 0.5 |
| Total | 140 | 100 |

The invention claimed is:

1. A co-micronization product comprising:
an active ingredient, wherein the active ingredient is ulipristal acetate, and
a surfactant, wherein the surfactant is a dodecyl sulphate salt, wherein the co-micronization product is obtained by co-micronizing the surfactant with the active ingredient, and wherein the weight ratio of the active ingredient to the surfactant ranges from 0.5 to 4.

2. The co-micronization product of claim 1, wherein the weight ratio of the active ingredient to the surfactant ranges from 0.5 to 2.5.

3. The co-micronization product of claim 1, wherein the surfactant is sodium dodecyl sulphate.

4. The co-micronization product of claim 1, having
a d50 of less than 20 μm, and/or
a d90 of less than 50 μm.

5. A method for preparing the co-micronization product of claim 1, comprising the steps of:
a) providing an active ingredient, wherein the active ingredient is ulipristal acetate,
b) mixing the active ingredient of step a) with a surfactant, wherein the surfactant is a dodecyl sulphate salt, to form a mixture, and
c) co-micronizing the mixture in step b) to obtain the co-micronization product, wherein the weight ratio of the active ingredient to the surfactant ranges from 0.5 to 4.

6. The method of claim 5, wherein in step a), the active ingredient is provided in a non-micronized form or a micronized form.

7. A pharmaceutical composition comprising the co-micronization product of claim 1 and a pharmaceutically acceptable excipient.

8. The pharmaceutical composition of claim 7, wherein the pharmaceutically acceptable excipient is selected from the group consisting of a diluent, a binder, a flow agent, a lubricant, a disintegrant and mixtures thereof.

9. The pharmaceutical composition of claim 7, comprising:
from 0.5% to 80% of co-micronization product,
from 0% to 10% of disintegrant,
from 15% to 95% of diluent, and
from 0% to 5% of lubricant,
the percentages being expressed by weight relative to the total weight of the composition.

10. The pharmaceutical composition of claim 7, which comprises from 1 mg to 100 mg of active ingredient per dose unit.

11. The pharmaceutical composition of claim 7, which is suitable for oral administration.

12. The pharmaceutical composition of claim 7, which is in the form of a powder, a granule, a coated tablet, an uncoated tablet, or a capsule.

13. A method for providing contraception to a subject comprising administering to said subject the co-micronization product of claim 1 or a pharmaceutical composition thereof.

14. A method for treating a gynaecological disorder in a subject comprising administering to said subject the co-micronization product of claim 1 or a pharmaceutical composition thereof.

15. The co-micronization product of claim 1, wherein the surfactant is selected from the group consisting of alkali metal salts of dodecyl sulphate, alkaline-earth metal salts of dodecyl sulphate, and combinations thereof.

16. The pharmaceutical composition of claim 8, wherein the disintegrant is selected from the group consisting of sodium croscarmellose, crospovidone and combinations thereof.

17. The pharmaceutical composition of claim 8, wherein the diluent is selected from the group consisting of lactose, hydrated lactose, mannitol, hydrated mannitol, microcrystalline cellulose, hydrated microcrystalline cellulose, and combinations thereof.

* * * * *